(12) United States Patent
Turner

(10) Patent No.: US 6,288,275 B1
(45) Date of Patent: Sep. 11, 2001

(54) SEPARATION AND PURIFICATION OF CARBOXYLIC ACIDS FROM FERMENTATION BROTHS

(75) Inventor: Stephen W. Turner, Hamilton, OH (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 09/350,244

(22) Filed: Jul. 9, 1999

(51) Int. Cl.$^7$ ..................................... C07C 51/42
(52) U.S. Cl. ................. 562/593; 562/590; 435/145; 435/142
(58) Field of Search ................... 435/142, 145; 562/580, 593, 590

(56) References Cited

U.S. PATENT DOCUMENTS

| | | |
|---|---|---|
| 4,282,323 | 8/1981 | Yates . |
| 4,407,953 | * 10/1983 | DeZeeuw et al. . |
| 5,254,466 | * 10/1993 | Pictaggio et al. . |
| 5,620,878 | 4/1997 | Picataggio et al. . |
| 5,962,285 | 10/1999 | Anderson et al. . |

OTHER PUBLICATIONS

WO 009521145 A2. Chen et al. (1995). Fermentation production of long chain alpha, omega–dicarboxylic acids from alkanes by use of a microorganism.*

GB 2,031,885 A. Furuhashi et al. (1980). Microbiological production of carboxylic acid mixtures containing w, (w–1)–dihydroxy carboxylic acids.*

* cited by examiner

Primary Examiner—Paul J. Killos
Assistant Examiner—Mahreen Chaudhry
(74) Attorney, Agent, or Firm—John E. Drach; Peter DeLuca; Susan L. Hess

(57) ABSTRACT

Carboxylic acids, particularly dicarboxylic acids, are separated from a fermentation broth by adjusting the pH of the fermentation broth to about 2.0 or below, and then heating the broth to a temperature sufficient to cause formation of three immiscible phases, one of which is an organic phase containing the carboxylic acids.

36 Claims, No Drawings

SEPARATION AND PURIFICATION OF CARBOXYLIC ACIDS FROM FERMENTATION BROTHS

BACKGROUND OF THE INVENTION

1. Field of the Invention

The present invention relates to a novel method for separating and purifying carboxylic acids, particularly long chain dicarboxylic acids, from fermentation broths, and to improved methods for producing carboxylic acids by fermentation.

2. Background of the Related Prior Art

Carboxylic acids, particularly long chain dicarboxylic acids are commercially important products utilized in the production of polymers, adhesives, perfumes, and antibiotics. As is known, production of dicarboxylic acids on an industrial scale typically occurs by fermentation with various microorganisms, e.g., yeast, using alkanes or fatty acids as the carbon source. The broth obtained from fermentation generally contains a significant amount of impurities such as the biomass from spent microorganisms, proteins, amino acids, fatty acids, sugars, carbohydrates, etc.

Several techniques exist for separating carboxylic acids from the various impurities present in the fermentation broth. For example, U.S. Pat. No. 4,075,093, describes a process of separating citric acid and isotropic acid from fermentation broths using membranes of selective permeability composed of polysulfones modified by acid groups, or of vinyl polymers which are chemically modified by acid or basic groups, within a particular pressure range.

U.S. Pat. No. 4,904,389 describes a process for separating saturated dicarboxylic acids from their mono and di-unsaturated analogs present in a fermentation broth using a membrane filtration system at a pressure of up to 20 bar and adjusting the pH of the fermentation broth to a pH of from 4 to 11, such that the membrane is selectively impermeable to at least one of the dicarboxylic acids present in the fermentation broth.

While the aforementioned membrane filtration methods may be useful in separating carboxylic acids from fermentation broths, such methods are time-consuming and require the prior separation of microorganism cells from the aqueous portion of the fermentation broth using various techniques such as filtration, centrifugation, etc.

Carboxylic acids may also be separated from other impurities in the fermentation broth by techniques involving separation of the biomass from the fermentation broth, precipitation of the carboxylic acid from the fermentation broth, and recovery of the crystals from the broth. For example, U.S. Pat. No. 5,612,131 describes a process for recovering organic acids, particularly citric acid, from fermentation broth by removing the biomass of spent microorganism cells and treating the cell-free broth with a strong acid or salt to precipitate out the organic acid, followed by separating the crystals to recover the organic acid.

U.S. Pat. No. 4,339,536 describes the separation of long chain dicarboxylic acids from a fermentation broth by adding diatomaceous earth to the fermentation broth, filtering the broth under pressure, and then precipitating the dicarboxylic acid from the broth using a mineral acid and heating.

JP No. 176498 describes the separation of dicarboxylic acids from fermentation broth by removing the biomass from the broth, heating and treating the cell-free broth with activated carbon, regulating the pH of the broth to below 4.0 using an inorganic acid, and recovering the crystallized dicarboxylic acid from the broth.

JP No. 086443 describes the refining of dicarboxylic acids from fermentation broth, which includes separating the biomass from the fermentation broth, heating the cell-free broth at a pH above 7.0, regulating the pH to below 3.0 using an inorganic acid, and recovering the dicarboxylic acid crystals.

The aforementioned processes requiring precipitation of the carboxylic acid from the fermentation broth are inefficient in that the precipitation process itself is time-consuming and requires the prior separation of the spent microorganism cells from the broth. Further, the crystals obtained from the precipitation process yield a less purified product than is desired.

Accordingly there continues to be a need for improved methods to efficiently separate carboxylic acids, particularly dicarboxylic acids, from a fermentation broth on an industrial scale to yield a substantially pure product at high yields and at reasonably low operating costs.

SUMMARY OF THE INVENTION

The present invention is directed to a method for separating carboxylic acids from a fermentation broth. The method comprises adjusting the pH of the fermentation broth to about 2.0 or below, and heating the acidified fermentation broth to a temperature sufficient to cause formation of three immiscible phases, wherein one of the three phases is an organic phase which contains the carboxylic acids.

Another aspect of the present invention is an improved method for producing carboxylic acids by fermentation. The method comprises fermenting with a microorganism in a culture medium including a nitrogen source, an organic substrate and optionally a co substrate to provide a fermentation broth, and adjusting the pH of the fermentation broth to about 2.0 or below. The acidified fermentation broth is then heated to a temperature sufficient to cause formation of three immiscible phases, wherein one of the three phases is an organic phase which contains the carboxylic acids.

Quite advantageously, the present process for separating carboxylic acids from an impure fermentation broth does not require the prior separation of the biomass of spent cells from the liquid portion of the fermentation broth, or the precipitation of the carboxylic acid from the cell-free broth. Instead, the whole fermentation broth containing spent microorganism cells is acidified using a strong mineral acid, which results in the liberation of salts from the carboxylates formed during the fermentation process, to yield free carboxylic acids. The acidified broth, upon heating, separates into three immiscible phases, namely, an organic phase containing substantially pure, free carboxylic acids, an aqueous phase containing some spent cells, and a solid phase containing mostly spent cells. The organic phase containing substantially pure carboxylic acids can be easily separated from the other two phases to provide substantially pure carboxylic acids in high yield, i.e., yield of about 70 to about 100% by weight.

Accordingly, the presently claimed method for separating carboxylic acids from an impure fermentation broth provides a high purity product, reasonably low operating costs and an increase in productivity resulting from the reduction in the amount of time required to separate the carboxylic acids.

As used herein, the term "fermentation broth" refers to the broth obtained after completion of fermentation and/or bioconversion by a microorganism in a culture medium which includes a nitrogen source, an organic substrate, and optionally a co substrate.

As used herein, the term "carboxylic acids" refers to compounds possessing one or more carboxyl groups. The term "polycarboxylic acids" refers to compounds possessing two or more carboxyl groups.

Other than in the claims and in the operating examples, or where otherwise indicated, all numbers expressing quantities of ingredients or reaction conditions used herein are to be understood as modified in all instances by the term "about".

DESCRIPTION OF THE PREFERRED EMBODIMENTS

The carboxylic acids to be separated from the fermentation broth may be monocarboxylic acids, or polycarboxylic acids. Preferably, the polycarboxylic acids are dicarboxylic acids. Examples of suitable dicarboxylic acids include, but are not limited to, 9-octadecenedioic acid, octadecanedioic acid, tetradecanedioic acid, dodecanedioic acid, hexadecanedioic acid, hexadecenedioic acid, heptadecanedioic acid, eicosanedioic acid and eicosenedioic acid, tridecanedioic acid, pentadecanedioic acid and combinations thereof.

Production of carboxylic acids by fermentation with various microorganisms is well known to those skilled in the art as described more fully herein below. U.S. Pat. Nos. 5,254,466, 5,648,247, and 5,620,878, the contents of each of which are incorporated by reference herein, describe procedures for producing carboxylic acids via fermentation which can be advantageously employed in the practice of the present invention. Typically, such procedures involve fermenting with a microorganism, e.g., yeast, in a culture medium which includes a nitrogen source, an organic substrate, and optionally a co substrate. The broth resulting from the fermentation will include product carboxylic acids in combination with a significant amount of impurities, e.g., biomass from spent microorganisms, proteins, amino acids, fatty acids, sugars, carbohydrates, and the like.

Once fermentation is completed, separation of carboxylic acids from the fermentation broth is initiated by adjusting the pH of the fermentation broth using a strong mineral acid. Typically, the pH of the fermentation broth prior to adjustment with mineral acid ranges from about 4.0 to about 8.5. The pH of the broth is adjusted to about 2.0 or below, and preferably, from about 2.0 to about 1.0. Suitable examples of strong mineral acids include, but are not limited to, hydrochloric acid, sulfuric acid, phosphoric acid, and bromic acid.

The acidified fermentation broth is then heated to a temperature of from about 60 to about 105° C. for about 2 minutes to about 2 hours to yield three immiscible phases: an organic phase containing a major amount of carboxylic acids and a minor amount of unreacted organic substrate and reaction by-products, an aqueous phase containing some yeast cells, and a solid phase containing mostly spent cells, e.g., yeast. Subsequently, the heated, acidified fermentation broth is optionally cooled to about 60 to about 98° C. and optionally centrifuged to enhance formation of a top organic phase containing carboxylic acids, a middle aqueous phase containing some cells, and a bottom solid phase containing spent cells. The top organic phase containing carboxylic acids is then quantitatively separated from the remaining two phases by any convenient method, e.g., suction of the upper phase using a vacuum, skimming, decanting, pumping, and the like.

To enhance phase separation, an organic solvent may be added to the fermentation broth prior to, during or subsequent to adjusting the pH of the broth. Suitable solvents are those with minimum water solubility and maximum solubility of the carboxylic acid in the organic phase. Suitable organic solvents include, but are not limited to, aliphatic hydrocarbons, aromatic hydrocarbons, aldehydes, ketones, ethers, alcohols, esters, acids, amides, amines and halogenated hydrocarbons. Once the top organic phase is separated from the other two phases, the other two phases can be washed with additional organic solvent, and centrifuged to remove any residual carboxylic acids remaining in the aqueous and solid phases. The washings containing residual carboxylic acids are then combined with the organic phase previously obtained as described above.

The organic phase is then washed with water to remove any traces of strong mineral acid, dried, and distilled under vacuum using stripping steam. The distillation is controlled to allow separation of the organic solvent, any unreacted starting materials, and any residue, e.g., triglycerides, wax esters, free acids, and anhydrides, from the product carboxylic acids. If desired, recovered unreacted starting materials and organic solvents can be recycled into the fermentation process for re-use.

The carboxylic acids obtained upon distillation may be further treated by additional purification procedures such as solvent crystallization, solvent extraction and melt crystallization.

Another embodiment of the present invention provides a method of producing carboxylic acids which comprises fermenting with a microorganism in a culture medium which includes a nitrogen source, an organic substrate, and optionally a co substrate to provide a fermentation broth. The pH of the resulting fermentation broth is adjusted to about 2.0 or below, followed by heating the acidified broth to a temperature sufficient to cause the formation of three immiscible phases, wherein one of the phases is an organic phase which contains the carboxylic acids.

The microorganism can be any microorganism which is capable of biologically oxidizing an organic substrate to a compound possessing one or more carboxyl groups. Typically, such a microorganism will be a bacterium or a yeast. Several strains of yeast are known to excrete alpha, omega-dicarboxylic acids as a byproduct when cultured on alkanes or fatty acids as the carbon source. These strains are set forth in U.S. Pat. No. 5,254,466. Preferably, the microorganism is a partially or completely beta-oxidation blocked species of Candida. More preferably, the Candida species is a *C. tropicalis* cell which has been genetically modified so that one or more of the chromosomal POX4A, POX4B and both POX5 genes have been disrupted. The substrate flow in these strains is either partially or completely redirected to the omega-oxidation pathway as the result of the partial or complete functional inactivation of the competing beta-oxidation pathway which results from POX gene disruption. Partial or complete disruption of the beta-oxidation pathway can also be achieved by blocking other enzymatic steps of that pathway. These strains may also have one or more cytochrome P450 monooxygenase (CYP) and/or NADPH-cytochrome reductase (CPR) genes amplified which result in an increase in the amount of rate-limiting omega-hydroxylase through CYP and/or CPR gene amplification and an increase in the rate of substrate flow through the omega-oxidation pathway. Examples of strains of *C. tropicalis* which are partially beta-oxidation blocked include, H41, H41B, H51, H45, H43, H53, H534, H534B and H435 as described in U.S. Pat. No. 5,254,466. An example of a completely beta-oxidation blocked strain of C. tropicalis, wherein all four POX4 and POX5 genes are disrupted by a URA3 selectable marker, is H5343 (ATCC 20962) as described in U.S. Pat. No. 5,254,466. Examples of C. tropicalis strains which are completely beta-oxidation blocked and which contain one or more CYP and/or CPR genes include A2, A4, A1, R20, R12, R24, AR25, AR40, AR42, COR34, and COR5 as described in U.S. Pat. No. 5,648,247; and HDC1, HDC5, HDC10-1, HDC10-2, HDC15, HDC20-1, HDC20-2, HDC20-3, HDC23-1, HDC23-2 and HDC23-3 as described in U.S. application Ser. No. 09/302,620 filed Apr. 30, 1999, the contents of which are incorporated by reference herein. Preferred strains of C. tropicalis are H5343, AR40, R24, HDC1 and HDC23-3. Strain AR40 (ATCC 20987) is a C. tropicalis cell which is an amplified H5343 strain wherein all POX4 genes and both copies of the chromosomal POX5 genes are disrupted by a URA3 selectable marker and which also contains three additional copies of a CYP gene, and two additional copies of a CPR gene. Strain R24 is an amplified H5343 strain in which all POX4 genes and both copies of the chromosomal POX5 genes are disrupted by a URA3 selectable marker and which also contains multiple copies of a CPR gene. HDC1 is an amplified H5343 strain which contains multiple copies of a CYP gene and HDC23-3 is an amplified H5343 strain which contains multiple copies of a CYP gene and a CPR gene integrated in the same orientation.

The fermentation medium can contain any inorganic or organic source of nitrogen normally used in methods for fermenting with microorganisms. Suitable inorganic nitrogen sources include, but are not limited to, alkali metal nitrates such as sodium or potassium nitrate, ammonium salts such as ammonium sulfate, ammonium chloride, ammonium nitrate, ammonium acetate, etc. Suitable organic sources include, but are not limited to, urea, corn steep liquor, yeast extracts, and other organic nitrogen sources known to those skilled in the art.

The organic substrate can be any aliphatic compound or mixtures thereof wherein at least one of the terminal carbons is a methyl group and which has from about 4 to about 22 carbon atoms. Such compounds include alkanes, alkenes, alkynes, carboxylic acids and their esters, and arenes. Preferred organic substrates are alkanes and carboxylic acids. Examples of suitable substrates include, but are not limited to, dodecane, tridecane, tetradecane, oleic acid, stearic acid, palmitic acid, myristic acid, methyl, ethyl or other esters of the aforementioned fatty acids and combinations thereof.

When producing a dicarboxylic acid, the organic substrate is preferably a compound possessing one carboxyl group and one methyl group or is a compound possessing one methyl group and a functional group that can be at least partially hydrolyzed to a carboxyl group. Thus, the organic substrate can be any aliphatic saturated or unsaturated monocarboxylic acid with a terminal methyl group except formic acid and acrylic acid. The organic substrate can also be an aromatic monocarboxylic acid possessing a methyl group, the simplest example of which is o, m, or p-methyl benzoic acid. Suitable monocarboxylic acids include, but are not limited to, oleic acid, stearic acid, palmitic acid, myristic acid, pelargonic acid, methyl benzoic acid and combinations thereof.

The use of oleic acid substrates having a high oleic acid content, i.e., substrates having an oleic acid content of equal to greater than 90% oleic acid produce a very viscous fermentation broth. Fermentation broths having high viscosities have relatively poor heat transfer and oxygen mass transfer. The use of oleic acid substrates having an oleic acid content of less than 90% result in fermentation broths that are less viscous thereby making the maintenance of proper temperature and dissolved oxygen levels much simpler. An example of such an oleic acid is technical grade oleic acid, the composition of which is set forth in the Example.

The method according to the invention permits the use of some monocarboxylic acids as substrates while avoiding the toxicity problem normally encountered with their use. Some monocarboxylic acids tend to be toxic to some microorganisms, particularly yeasts such as C. tropocalis, and especially beta-oxidation blocked C. tropocalis strains which have been genetically modified so that chromosomal POX4A, POX4B and both POX5 genes have been disrupted and/or those C. tropocalis strains wherein the one or more reductase genes have been amplified. As stated above, the present invention encompasses the use of a combination of monocarboxylic acids as the organic substrate. The relative amount of each monocarboxylic acid in combination will typically vary from 1/100 to 1/1 with the preferred amount being from 1/1 to 1/10. The amount for any particular fermentation will vary according to the relative toxicities of the monocarboxylic acids and will be readily ascertainable to those skilled in the art.

The organic substrate is preferably partially neutralized with an alkaline earth metal hydroxide prior to the addition of the substrate to the fermentation broth. It has been determined that the partial neutralization provides a more rapid induction of carboxylic acid production. The overall transformation time in the fermentor is thereby reduced, thus resulting in improved turn-around times in the fermentor and an overall increase in productivity. The optimum degree of partial neutralization will typically vary from 1 to 10%, and preferably will vary from 1 to 2.5%, but can be any value from one part per million to 99% depending upon the fermentation conditions, the nature of the substrate, co substrate, the microorganism and the carboxylic acids formed in the fermentation. The optimum degree of partial neutralization can be readily determined by those skilled in the art. The preferred alkaline earth metal hydroxides are calcium and magnesium hydroxide.

There is an advantage to adding the organic substrate in increments as opposed to an all-in method. In the incremental addition method, the total charge of organic substrate is divided into a plurality of smaller amounts each of which is added to the fermentation broth on a regular basis. The advantage gained by the incremental addition is that the rate of production of carboxylic acid remains essentially constant as opposed to an ever decreasing rate observed with the all-in method. The amount of organic substrate added in each increment and the time between additions will vary depending upon the fermentation conditions, the nature of the organic substrate, the co substrate, the microorganism, and the carboxylic acids formed in the fermentation. Appropriate incremental addition parameters can be readily determined by those skilled in the art.

The optional co substrate is selected from the group consisting of glucose, fructose, maltose, glycerol and sodium acetate. The preferred co substrate is glucose. A co substrate is necessary when fermenting with particular strains of yeast such as C. tropicalis H5343 as described above, wherein the beta-oxidation pathway of these strains is totally blocked, and energy is not available from the oxidation of the substrate. Co substrate added at a definite rate along with the substrate strikes a balance between providing an energy source for the cells which allow the partial oxidation of the substrate to alpha, omega-dicarboxylic acids.

After fermentation has substantially completed, the pH of the resulting fermentation broth is adjusted and the pH adjusted broth is heated to a temperature sufficient to cause the formation of three immiscible phases, as described in detail above. Thereafter, the product carboxylic acids are recovered as described in detail above.

The following example is meant to illustrate but not to limit the invention.

EXAMPLE

Separation Of Dicarboxylic Acids Produced From Fermentation Of Oleic Acid With Strain H5343 (ATCC 20962)

A fermentor was charged with a semi-synthetic growth medium having the composition 70 g/l glucose (anhydrous, 6.7 g/l Yeast Nitrogen Base (Difco Laboratories)), 3 g/l yeast extract, 3 g/l ammonium sulfate, 2 g/l monopotassium phosphate, and 0.04 g/l ferrous sulfate. Components were made as concentrated solutions for autoclaving, then added to the fermentor upon cooling: final pH approximately 5.2. This charge was inoculated with 5–10% of an overnight culture of *C. tropocalis* H5343 prepared in YM medium (Difco Laboratories) as described in the methods of Examples 17 and 20 of U.S. Pat. No. 5,254,466. Cells were then cultivated to about 15–35 g dry weight/i limited by the available nitrogen in the medium. There was a slight stoichiometric excess amount of glucose in the above charge that remained for about 1–3 hours after depletion of nitrogen sources. Air and agitation were supplied to maintain the dissolved oxygen at greater than about 40% of saturation versus air. Lower dissolved oxygen resulted in substantial in situ accumulation of partial glucose-catabolic products, primarily ethanol. The pH was maintained at about 5 by the addition of 5N KOH. About 200 g of technical grade oleic acid having the following composition: 0.30% $C_{12}$; 2.4% $C_{14:1}$; 4.7% $C_{16:1}$; 4.6% $C_{16:1}$; 0.20% $C_{17}$; 0.80% $C_{18}$; 69.9% $C_{18:1}$; 10.50% $C_{18:2}$; 0.30% $C_{18:3}$ saponified with calcium hydroxide was added and the glucose co substrate feed (1.8 g/l/hr) was started near the time the culture entered stationary phase to initiate omega oxidation. Two successive charges of 250 g of technical grade oleic acid saponified with calcium hydroxide were added. The second 250 g charge was added about 23 hours after the initial 250 g charge. The fermentation was continued until gas/liquid chromatography (GLC) analysis showed an oleic acid content of less than 1 g/Kg at which time the fermentation broth was placed in a 70° C. oven.

A sample of the fermentation broth (2540.9 g) produced as described above was placed in a 5 liter flask, stirred and heated to approximately 50° C. Concentrated $H_2SO_4$ (49.83 g) was added slowly to the heated fermentation broth until the pH of the broth was 1.5. The acidified fermentation broth was then heated to reflux for 1 hour (100° C.). The acidified fermentation broth was then centrifuged at 10,000 rpm for 10 minutes to yield three immiscible phases: a top organic phase, a middle aqueous phase, and a bottom solid phase. Dibasic acids were quantified by extracting the whole fermentation broth, methyl esterifying the extract, and analyzing for dibasic acid methylesters by GLC. The acidified, heated fermentation broth was found to contain 9-octadecenedioic acid (32.6 g).

The top organic phase (61.85 g) was collected, washed with water, and left overnight in a hood. GLC analysis indicated that the top organic phase contained 80.6% by weight 9-octadecenedioic acid. A sample of the top organic phase was distilled to yield three fractions, a top distillate, main distillate, and residue fraction.

The top distillate fraction (10.7 g) contained approximately 17.6% by weight 9-octadecenedioic acid. The main distillate fraction (29.8 g) contained 87.8% by weight 9-octadecenedioic acid. Infra-red and nuclear magnetic analysis of the residue fraction (16.7 g) indicated that the residue fraction contained mostly triglycerides, wax esters, free acid, and anhydrides.

The aqueous phase contained an upper layer of yeast cells suspended between the water and organic phase. GLC analysis of the aqueous phase indicated only trace amounts (approximately 0.3 g) of oleic and dicarboxylic acids. The bottom cell phase contained 9-octadecenedioic acid (78.7 g/l).

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed:

1. A method for separating carboxylic acids from a fermentation broth comprising the steps of
   (a) adjusting the pH of the fermentation broth to about 2.0 or below; and
   (b) heating the acidified fermentation broth of step (a) to a temperature sufficient to cause formation of three immiscible phases, wherein one of the three phases is an organic phase which contains the carboxylic acids.

2. The method according to claim 1 wherein the carboxylic acids are polycarboxylic acids.

3. The method according to claim 2 wherein the polycarboxylic acids are dicarboxylic acids.

4. The method according to claim 3 wherein the dicarboxylic acids are selected from the group consisting of 9-octadecenedioic acid, octadecanedioic acid, tetradecanedioic acid, dodecanedioic acid, hexadecanedioic acid, hexadecenedioic acid, heptadecanedioic acid, eicosanedioic acid, eicosenedioic acid, tridecanedioic acid, pentadecanedioic acid and combinations thereof.

5. The method according to claim 1 wherein the pH of the fermentation broth is adjusted to about 2.0 to about 1.0.

6. The method according to claim 5 wherein the pH of the fermentation broth is adjusted with a strong mineral acid selected from the group consisting of hydrochloric acid, sulfuric acid, phosphoric acid and bromic acid.

7. The method of claim 1 further comprising centrifuging the heated, acidified fermentation broth to cause the three immiscible phases to separate into a top phase, middle phase and bottom phase.

8. The method of claim 7 wherein the top phase contains the carboxylic acids.

9. The method of claim 1 wherein the organic phase containing the carboxylic acids is separated from the two other phases.

10. The method of claim 7 wherein the top phase is separated from the middle and bottom phases.

11. The method of claim 9 wherein the organic phase is separated from the two other phases by a method selected from the group consisting of suction, skimming, decanting and pumping.

12. The method according to claim 1 further comprising the addition of an organic solvent prior to, during or subsequent to step (a).

13. The method according to claim 12 wherein the organic solvent is selected from the group consisting of aliphatic hydrocarbons, aromatic hydrocarbons, aldehydes, ketones, ethers, alcohols, esters, acids, amides, amines and halogenated hydrocarbons.

14. The method according to claim 1 wherein the temperature is from about 60 to about 105° C.

15. The method according to claim 9 further comprising drying and distilling the separated organic phase to separate the carboxylic acids from unreacted starting materials and residue containing reaction by-products.

16. A method for producing carboxylic acids comprising the steps of:

(a) fermenting with a microorganism in a culture medium comprising a nitrogen source, an organic substrate and optionally a co substrate to provide a fermentation broth;

(b) adjusting the pH of the fermentation broth to about 2.0 or below; and (c) heating the acidified fermentation broth of step (b) at a temperature sufficient to cause formation of three immiscible phases, wherein one of the three phases is an organic phase which contains the carboxylic acids.

17. The method according to claim 16 wherein the microorganism is a partially or completely beta-oxidation blocked *C. tropocalis* cell.

18. The method according to claim 17 wherein the microorganism is a completely blocked *C. tropocalis* cell wherein both copies of the chromosomal POX5 gene and the chromosomal POX4A and POX4B genes are disrupted.

19. The method according to claim 18 wherein the microorganism is *C. tropicalis* strain H5343.

20. The method according to claim 16 wherein the carboxylic acids are polycarboxylic acids.

21. The method according to claim 20 wherein the polycarboxylic acids are dicarboxylic acids.

22. The method according to claim 21 wherein the dicarboxylic acids are selected from the group consisting of 9-octadecenedioic acid, octadecanedioic acid, tetradecanedioic acid, dodecanedioic acid, hexadecanedioic acid, hexadecenedioic acid, heptadecanedioic acid, eicosanedioic acid, eicosenedioic acid, tridecanedioic acid, pentadecanedioic acid and combinations thereof.

23. The method according to claim 16 wherein the organic substrate is an alkane.

24. The method according to claim 16 wherein the organic substrate is a monocarboxylic acid.

25. The method according to claim 24 wherein the monocarboxylic acid is oleic acid, stearic acid, palmitic acid, myristic acid, pelargonic acid, methyl benzoic acid and combinations thereof.

26. The method according to claim 16 wherein the pH of the fermentation broth is adjusted to about 2.0 to about 1.0.

27. The method according to claim 16 wherein the pH of the fermentation broth of step (b) is adjusted by a strong acid selected from the group consisting of hydrochloric acid, sulfuric acid, phosphoric acid and bromic acid.

28. The method of claim 16 further comprising centrifuging the heated, acidified broth to cause the three immiscible phases to separate into a top phase, middle phase and bottom phase.

29. The method of claim 28 wherein the top phase contains the carboxylic acids.

30. The method of claim 16 wherein the organic phase containing the carboxylic acids is separated from the two other phases.

31. The method of claim 28 wherein the top phase is separated from the middle and bottom phases.

32. The method of claim 30 wherein the organic phase is separated from the two other phases by a method selected from the group consisting of suction, skimming, decanting and pumping.

33. The method according to claim 16 further comprising the addition of an organic solvent prior to, during or subsequent to adjusting the fermentation broth of step (a).

34. The method according to claim 33 wherein the organic solvent is selected from the group consisting of aliphatic hydrocarbons, aromatic hydrocarbons, aldehydes, ketones, ethers, alcohols, esters, acids, amides, amines and halogenated hydrocarbons.

35. The method according to claim 16 wherein the temperature is from about 60 to about 105° C.

36. The method according to claim 31 further comprising drying and distilling the separated organic phase to separate the carboxylic acids from unreacted starting materials and from residue containing reaction by-products.

* * * * *